(12) United States Patent
Manni et al.

(10) Patent No.: US 8,985,996 B2
(45) Date of Patent: Mar. 24, 2015

(54) DEVICE FOR FORMING CONCRETE SPECIMENS

(75) Inventors: Enrico Manni, Fiorenzuola d'Arda (IT); Paolo Fila Robattino, Strona (IT); Luca Borotti, Quarona Sesia (IT)

(73) Assignee: Betonrossi S.p.A., Piacenza (IT)

( * ) Notice: Subject to any disclaimer, the term of this patent is extended or adjusted under 35 U.S.C. 154(b) by 0 days.

(21) Appl. No.: 14/127,632

(22) PCT Filed: Jun. 11, 2012

(86) PCT No.: PCT/IB2012/052944
§ 371 (c)(1),
(2), (4) Date: Dec. 19, 2013

(87) PCT Pub. No.: WO2012/176092
PCT Pub. Date: Dec. 27, 2012

(65) Prior Publication Data
US 2014/0120202 A1    May 1, 2014

(30) Foreign Application Priority Data
Jun. 22, 2011    (IT) .............................. PR2011A0058

(51) Int. Cl.
*B28B 1/087* (2006.01)
*B28B 5/08* (2006.01)
*B28B 13/02* (2006.01)
*G01N 1/28* (2006.01)
*B28B 7/00* (2006.01)

(52) U.S. Cl.
CPC ................ *G01N 1/286* (2013.01); *B28B 1/087* (2013.01); *B28B 13/0275* (2013.01); *B28B 13/02* (2013.01); *B28B 7/0094* (2013.01); *B28B 5/08* (2013.01); *G01N 1/28* (2013.01)
USPC ....................................................... 425/432

(58) Field of Classification Search
CPC ........ B28B 1/087; B28B 5/08; B28B 7/0094; B28B 13/02; B28B 13/0275
USPC ........... 425/62, 183, 185, 218, 219, 261, 432, 425/447, 453
See application file for complete search history.

(56) References Cited

U.S. PATENT DOCUMENTS

| | | | | |
|---|---|---|---|---|
| 2,494,212 A | * | 1/1950 | Spriggs et al. | ................ 425/219 |
| 2,499,209 A | * | 2/1950 | Balasquide | .................. 425/218 |
| 2,524,683 A | * | 10/1950 | Sumpf | ............................ 425/62 |
| 2,560,208 A | * | 7/1951 | Benischek | ..................... 425/432 |
| 2,598,254 A | * | 5/1952 | Grueneberg | .................... 425/421 |
| 4,557,681 A | * | 12/1985 | Wright et al. | ................... 425/62 |

(Continued)

FOREIGN PATENT DOCUMENTS

| | | | |
|---|---|---|---|
| DE | 27 37 186 | * | 5/1979 |
| FR | 1292939 | * | 9/1967 |
| GB | 421096 | * | 12/1934 |

(Continued)

*Primary Examiner* — James Mackey
(74) *Attorney, Agent, or Firm* — Pearne & Gordon LLP

(57) ABSTRACT

A device for forming concrete specimens including:
  a concrete tank and a discharge mouth (20);
  an element (33) rotating around a rotation axis suitable for supporting at least a first and/or a second form, the discharge mouth (20) and the force of gravity directing the concrete flowing out of the tank to the element (33);
  a wall-mounted vibrator (50) suitable for generating the vibration of at least the contents of first and/or second form.

12 Claims, 4 Drawing Sheets

(56) References Cited

U.S. PATENT DOCUMENTS 4,725,216 A * 2/1988 Foster ............................ 425/62
6,224,359 B1 * 5/2001 Domazet ........................ 425/62

FOREIGN PATENT DOCUMENTS

| JP | 61 083933 A | 4/1986 |
| WO | 2007/104293 A1 | 9/2007 |

* cited by examiner

DEVICE FOR FORMING CONCRETE SPECIMENS

The object of the present invention is a device for forming concrete specimens.

Concrete for structural use is subjected to acceptance tests (for which specific standards exist). Normally, when the concrete is cast it is commonly sampled in fresh state and is then placed in suitable forms, by means of which, once it has set, specimens for the subsequent tests are obtained.

For this purpose, a technician removes the fresh concrete from the truck mixer (pre-packaged concrete) or from a bucket (pre-fabricated concrete) or from the laboratory concrete mixer. Usually, the concrete is placed in a barrow, which is then moved to the pre-selected place to fill the single forms (this filling normally occurs in a position that is far from the filling point of the barrow; this allows, for example, filling to be carried out in a zone that is perfectly flat and horizontal). The concrete inside the single forms is then compacted by a needle vibrator or vibrating plate and lastly the concrete that bulges out from the open top of the form is levelled by a trowel.

This manner of proceeding is not without drawbacks linked to the specialised operator for performing all the sampling operations.

In this context, the technical task of the present invention is to propose a device for forming concrete specimens that overcomes the drawbacks of the prior art described above.

In particular, one important object of the present invention is to provide a device for forming concrete specimens that is able to facilitate the task of the operator, by increasing productivity and simplifying the task.

The defined technical task and the specified objects are substantially reached by a specimen forming device, comprising the technical features set out in one or more of the attached claims.

Further features and advantages of the present invention will appear more clearly from the indicative and therefore non-limiting description of a preferred but non-limiting embodiment of a specimen forming device illustrated in the attached drawings, in which.

Figure 1:
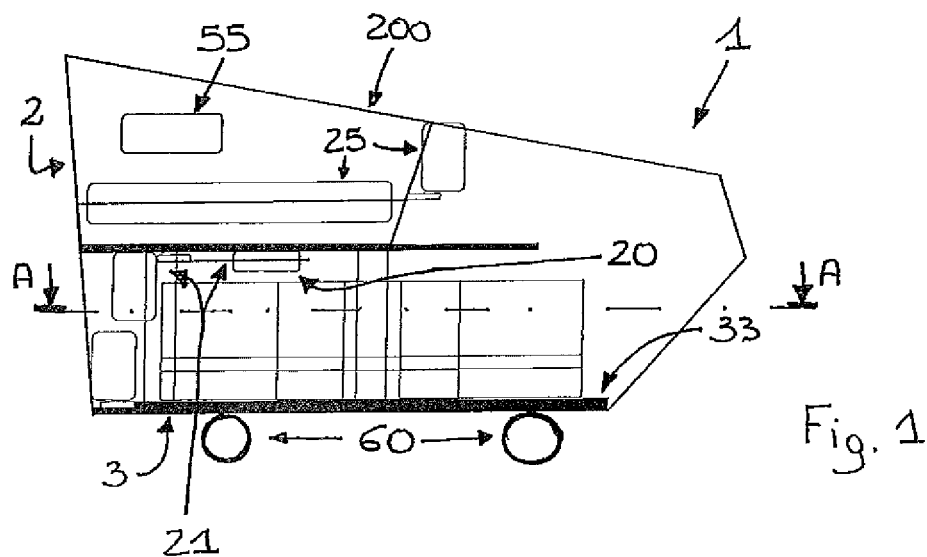
FIG. 1 shows a side view of the device for forming concrete specimens according to the present invention.
Figure 2:
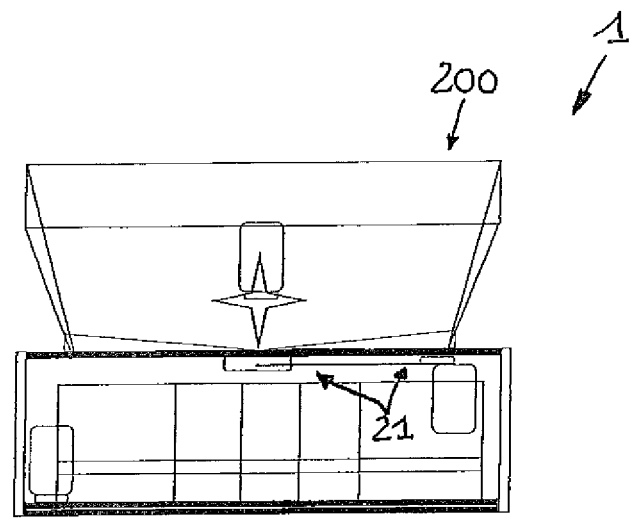
FIG. 2 shows a rear view of a device for forming concrete specimens according to the present invention.
Figure 3:
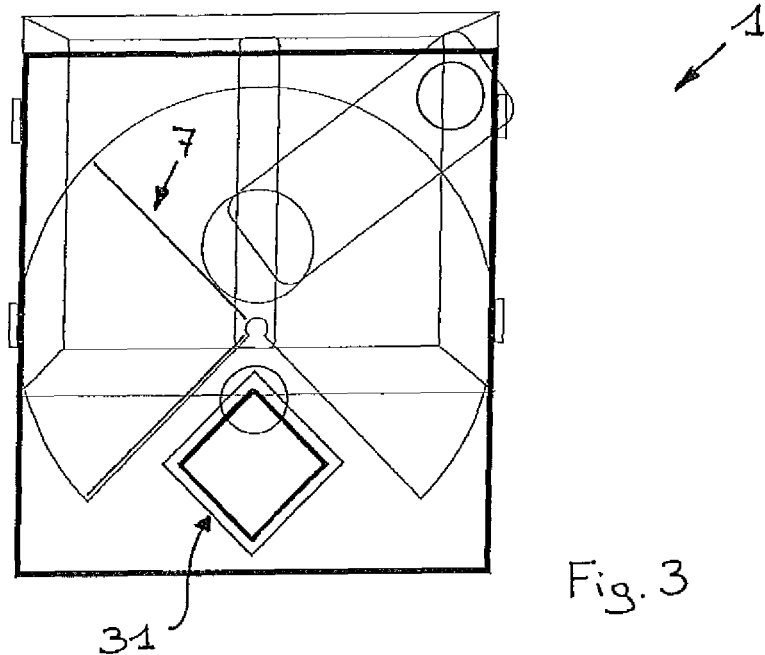
FIG. 3 shows a top view of the device for forming concrete specimens according to the present invention.
Figure 4:
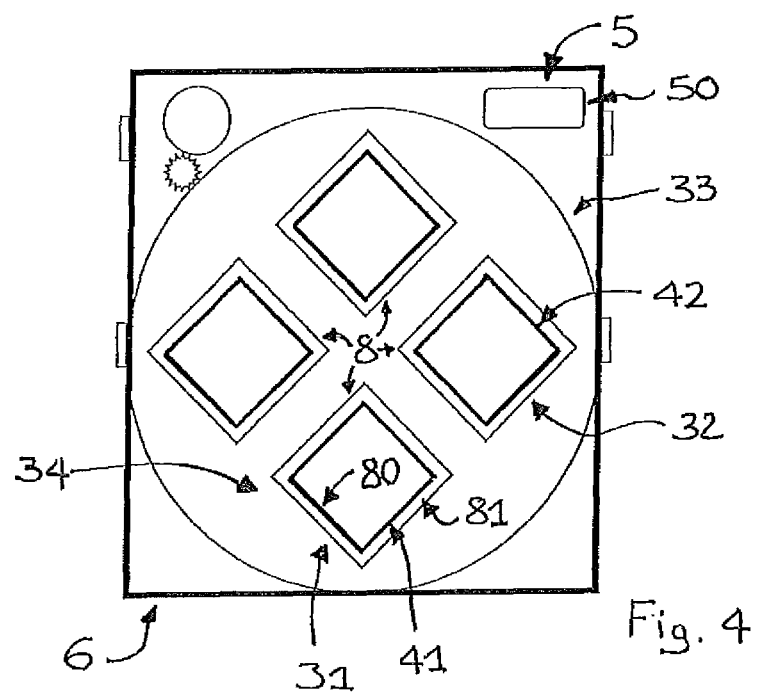
FIG. 4 shows a view according to the section plane A-A of FIG. 1.

In the attached figures, reference number 1 indicates a device for forming concrete specimens.

This device 1 comprises concrete feeding means 2 comprising a concrete discharge mouth 20. The feeding means 2 could comprise a tank intended for containing the concrete. This tank acts as a storage unit. This tank is typically a hopper 200.

The device 1 further comprises support means 3 suitable for supporting at least a first (and/or a second) form, said discharge mouth 20 and the force of gravity directing the concrete flowing out of the feeding means 2 to said support means 3.

The discharge mouth 20 is opportunely built into the hopper 200. In the preferred solution, the concrete coming out of the hopper is intended for entering a form directly. In an alternative constructional solution that is not shown the feeding means 2 also comprise a channel placed immediately downstream of the hopper 200 and at a greater height than the support means 3; in this case the discharge mouth 20 is integrated into said channel (in particular it is an end of said channel). This channel receives the concrete from the hopper 200 and conveys the concrete to the support 3.

The device 1 further comprises first vibrator means 5 suitable for generating the vibration of at least the contents of the first and/or of the second form.

Opportunely, the support means 3 could also support further forms. In the solution illustrated in the attached figures the support means 3 support four forms. The forms are opportunely removably connected to the support means 3. The forms could be reusable (for example made of plastic) or monouse (for example made of polystyrene).

The support means 3 comprise a first and a second zone 31, 32 that are suitable for supporting respectively a first and a second form. The feeding means 2 and said support means 3 are movable reciprocally to assume at least a first and a second configuration; in the first configuration the discharge mouth 20 and gravity direct the outflowing concrete towards said first zone 31, in the second configuration said discharge mouth 20 and gravity direct the outflowing concrete towards said second zone 32.

Preferably, in the first configuration said first zone is below said discharge mouth 20; in the first configuration the first zone 31 is thus along the vertical projection of the discharge mouth 20; in the second configuration said second zone 32 is below said discharge mouth 20; in the second configuration said second zone 32 is thus along the vertical projection of the discharge mouth 20.

The possibility of directing the concrete now to a first form and now to a second form also allows layered filling of the various forms, optimizing time, by vibrating the concrete between the formation of one layer and the next. In fact, with the device in the first configuration a first layer of concrete can be introduced into first form; subsequently, with the device in the second configuration a layer of concrete can be introduced into the second form and simultaneously vibrate the first layer in the first form. Subsequently, a second layer can be inserted into the first form and simultaneously the concrete in the second form can be vibrated and so on. This filling mode contributes, in synergy with the use of the above storage unit, to obtaining a more representative specimen of the concrete to be tested. In fact, filling in layers and the vibrations applied to each layer immediately after the introduction into the form facilitates the exiting of air (in this manner the air in fact has to traverse only the thickness of the single layer and not of the entire form). The presence of less air thus makes the specimen more representative of the quality of the concrete.

Further, the alternating of the layers in the first and in the second form improves distribution of the concrete in the storage unit such that the final specimen is more heterogeneous and thus more representative than the average values of the tested concrete.

Opportunely, the first vibrator means 5 comprise a wall-mounted vibrator 50 that vibrates said support means 3. The first vibrator means 5 could in addition or alternatively comprise a needle vibrator.

Figure 5B:
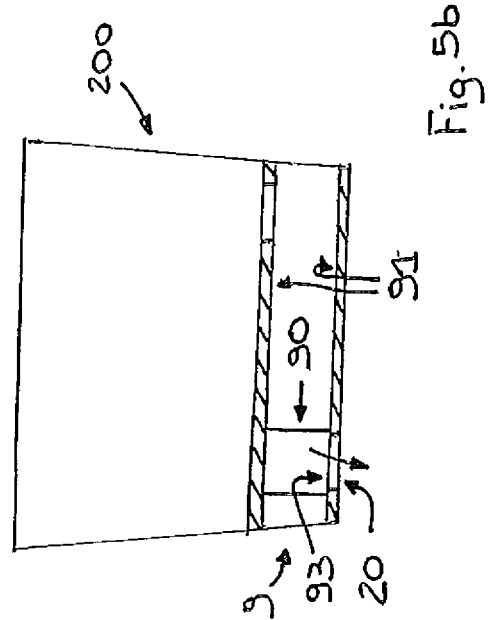
FIGS. 5a and 5b show in two distinct operating configurations a particular constructional solution of a component of a device according to the present invention.
Figure 5A:
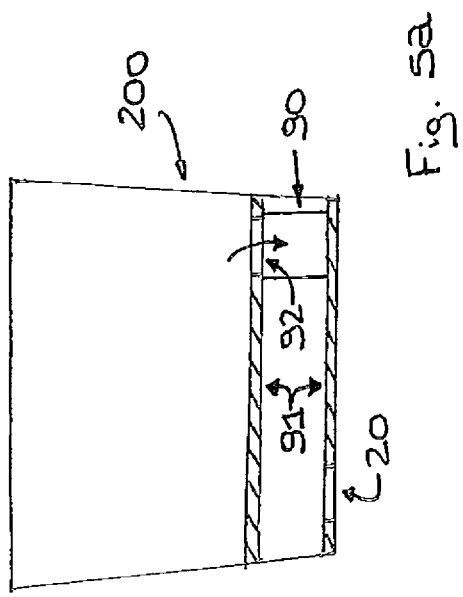

Advantageously, the hopper 200 comprises a homogenizer 25. Typically, this homogeniser is of mechanical type, for example blade type. The homogenizer protrudes inside said hopper 200. In the preferred solution, the hopper 200 comprises in the lower portion a valve 21 that permits or prevents the passage of the concrete through said discharge mouth 20. Preferably, the valve 21 is placed at said discharge mouth 20. Opportunely, said valve 21 is driven electrically. In the preferred solution this valve 21 is of the guillotine type. When the valve 21 is open the concrete flows through said discharge mouth 2 at least through the force of gravity. Opportunely, the feeding means 2 comprise dosing means 9 for dosing the amount of concrete to allow to flow through the discharge mouth 20. In one constructional solution the dosing means 9 could intervene by regulating the opening/closing intervals of the valve 21. In an alternative constructional solution the dosing means 9 could comprise a carriage 90 that is open above and below and is movable between a first and a second position along guiding means 91; in the first position (see FIG. 5a) of the carriage 90 the guiding means 91 have an upper opening 92 that places the carriage 90 in communication with a portion of the hopper 200 (or anyway a concrete storing unit) that acts as a tank for the concrete; still in the first position the guiding means 91 close the carriage 90 below; in the second position (see FIG. 5b) the guiding means 91 have a lower opening 93 that places the carriage in communication with the discharge mouth 20.

In one alternative constructional solution that is not illustrated the feeding means 2 comprise a tank for the concrete and a chamber that is in fluid communication with said discharge mouth 20. In this case the dosing means 9 could comprise means that transfer a set quantity of concrete from the tank to the chamber (for example until a set level of concrete in said chamber is reached).

Figure 6:
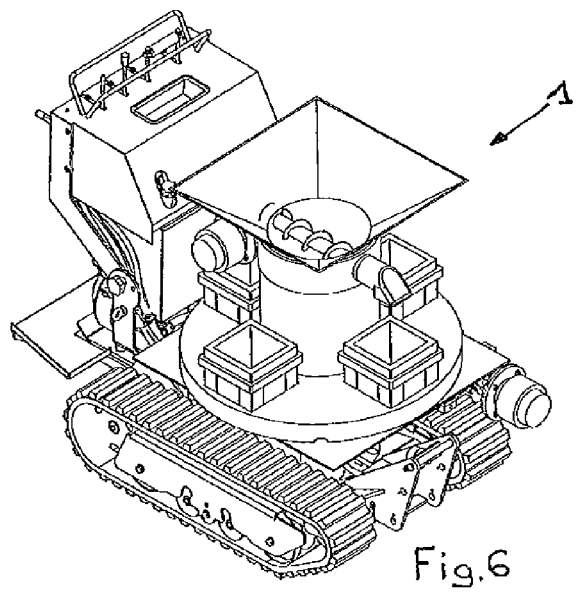
FIG. 6 shows a perspective view of a device according to the present invention.
Figure 8:
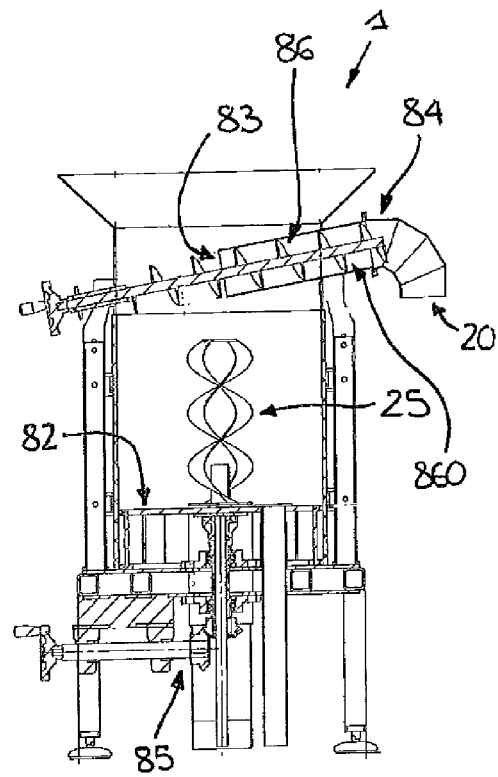
FIG. 8 shows a view according to the section plane A-A of FIG. 7.
Figure 7:
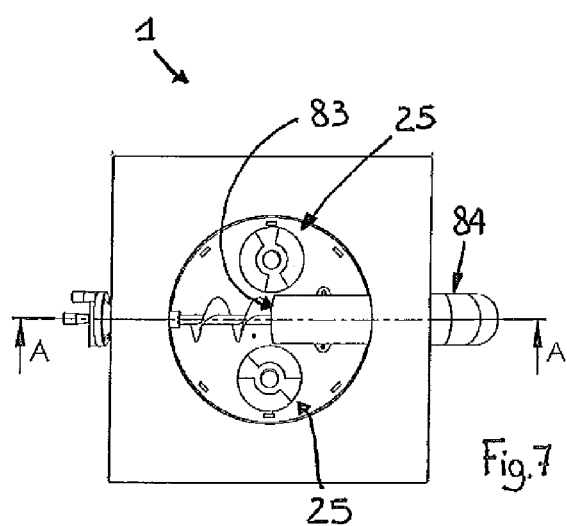
FIG. 7 shows a top view of a device according to the present invention.

In the constructional solution exemplified in FIGS. 6-8, the tank of the feeding means 2 comprises:
  a raisable and a lowerable lower bottom 82;
  an exit opening 83 for the concrete that lies on the bottom 82 of the tank and which is connectable to said discharge mouth 20 (typically through a conduit 84).

For this purpose, the device 1 comprises means 85 for raising/lowering the bottom 82 of the tank. Typically, the means 85 for raising/lowering the bottom 82 of the tank are fluidodynamic (for example they comprise one or more fluidodynamic pistons) but they could also be mechanical (see illustrated solution). The means 85 for raising/lowering the bottom 82 of the tank can be considered to be part of the dosing means 9. Advantageously, the homogenenizer 25 rises and lowers together with the lower bottom 82.

Opportunely, the exit opening 83 for the concrete lies at one end of said conduit 84; typically, the opening 83 and the discharge mouth 20 are at the ends of said conduit 84; the dosing means 9 further comprise means 86 for making the concrete advance along said conduit 84; for example the means 86 for making the concrete advance comprise a feed screw 860 that protrudes inside the conduit 84.

In the preferred solution the hopper 200 (or more in general the feeding means 2) comprises second vibrator means 55 that facilitate the flow of the concrete through said discharge mouth 20. The action of these second vibrator means 55 is additional to the gravity acting on the concrete and is particularly important if the concrete is particularly dense.

Opportunely, the capacity of the hopper 200 is such as to contain at least one volume that is greater than or the same as 30000 cm$^3$, preferably 33000 cm$^3$. This normally allows at least 8 specimens to be filled. The mouth of the hopper further comprises a protective grille. This feature is used to prevent a hand of the user passing through (for example the grille has a square mesh measuring 5 cm each side).

As illustrated by way of example in the attached figures, the device 1 advantageously comprises a weight-bearing structure 6 supporting the feeding means 2 (or at least the hopper 200) and the support means 3.

In a specific constructional solution the device 1 could be a fixed laboratory device. Alternatively, the weight-bearing structure 6 could comprise facilitated sliding means 60 suitable for allowing the movement of weight-bearing structure 6 on a surface outside the device 1. The facilitated sliding means 60 are illustrated only in FIGS. 1 and 6 (and have been omitted in the other figures). The facilitated sliding means 60 typically comprise wheels, but could comprise slides or tracked means. In this case, opportunely, the device 1 could be integrated into a carriage. In this case, the device 1 advantageously has dimensions that are such as to be enclosed inside an imaginary parallelpipedon measuring 1.5 meters×1 meter×1 meter. This in turn allows the positioning inside motor vehicles (for example utility vehicles) that facilitate the transfer thereof from one worksite to another.

The facilitated sliding means 60 could be motorized (even if this condition is optional). The device 1 could thus be integrated into a self-propelling motor vehicle. Advantageously, in this case the sliding means 60 could be driven by an electric motor or by an internal combustion engine. In the case of the use of an electric motor, a connection with batteries is provided that opportunely provides power for at least 8 hours; in the case of an internal combustion engine the device 1 comprises a tank that any way provides power for at least 8 hours. Advantageously, the device 1 comprises connecting means for connecting to the electric network to recharge possible batteries (or, if the device 1 is fixed, to supply the device 1 also in the absence of batteries).

The support means 3 comprise/coincide with an element 33 rotating around a rotation axis. Opportunely, the rotation axis is vertical. In this case, Advantageously, the hopper 200 is substantially fixed.

Opportunely, the device 1 could comprise a nozzle dispensing removing oil (in order to facilitate the extraction of the specimen from the form).

Opportunely, this nozzle is at the end of a flexible conduit. The user can thus handle this nozzle and this conduit to direct the outward jet inside the forms.

Alternatively the nozzle could be positioned on said support means 3 and the removing oil could be introduced inside the forms by gravity after the form has been positioned below the nozzle.

The device 1 further comprises a scraper 7. The scraper 7 is suitable for levelling the concrete that bulges out above said first and/or second form. Advantageously, this operation occurs at least during a complete rotation of said element 33 rotating about said rotation axis. For this purpose, the form moves together with the support means 3 underneath the scraper 7 that eliminates the excess concrete. In one alternative solution the form could remain fixed and the scraper 7 could be provided with an actuator that moves it (solution not illustrated). For this reason, the scraper 7 is positioned above said support means 3. Preferably, the height of the scraper 7 is adjustable in such a manner as to be able to adapt to forms of different dimensions. Alternatively, it is placed at a standard height, taking into account that normally the forms used have cubic dimensions with a side of 15 centimeters. In the preferred solution the scraper is made of plastic, typically polyurethane.

Opportunely, the support means 3 comprise a supporting base 34 on which at least said first and/or said second form (and possibly other forms) are intended to be rested.

For this purpose, the scraper 7 is placed about 15 centimeters above said supporting base 34 of the support means 3.

Opportunely, the device 1 comprises means 8 for positioning and at least partially retaining at least the first and/or the second form on top of said support means 3. The partial retention by the means 8 is due to the fact that they prevent lateral movements on the support means 3, but allow the form to be extracted upwards. Opportunely, said positioning and at least partial retaining means 8 allow the first and/or the second form to be retained during moving of said support means 3 or any way when the first vibrator means 5 are active (this is particularly important if said wall-mounted vibrator 50 is used to vibrate the support means 3).

Opportunely, the positioning and at least partial retaining means 8 comprise a first collar 80 suitable for at least partially framing said first form. The first collar 80 is advantageously at least partially removable from the supporting base 34 in order to facilitate the extraction from the first form. The first collar 80 is set at a distance from said supporting base 34. This allows the facilitated flow by gravity of liquid for washing the supporting base 34. Opportunely, means for positioning and at least partial retention of the third and of the fourth form are present.

The first collar 80 comprises a channel 81 suitable for collecting the concrete that comes out of the first form (opportunely, the channel could affect only one portion of the first collar).

Advantageously, a plurality of collars are present, each one of which is intended for retaining in position at least one corresponding form.

Preferably, said hopper 200 and said support means 3 are reciprocally movable to assume also a third configuration in which at least a part of the first zone 31 bulges externally outside the vertical projection of said hopper 200 on said support means 3 to facilitate the removal and positioning of said first form relative to the support means 3.

Advantageously, said support means 3 and/or said hopper 200 are overturnable to facilitate the disposal of a washing liquid that is usable for cleaning the device 1. In this case, the washing liquid that remains on walls of the device 1 could in fact be disposed of faster by gravity to prevent it gathering on the device 1. The weight-bearing structure 6 could comprise a first part on which the support means 3 and the hopper 200 are constrained. The device 1 could comprise a fluidodynamic piston that overturns said first part of the weight-bearing structure 6, said piston being interposed between said first part of the weight-bearing structure and at least a second part of the weight-bearing structure 6.

Advantageously, the forming device 1 comprises a positioning sensor of a form below said discharge mouth 20. Opportunely, the detecting of a form below the discharge mouth by said positioning sensor causes the arrest of the movement (in particular of the rotation) of said support means 3 and the opening of said valve 21.

Advantageously, the device 1 further comprises a level sensor that is suitable for determining the level of the concrete inside a form placed below said discharge mouth 20. The detecting by said level sensor of a level that is greater than or the same as a preset level causes a first procedure to start up that comprises one or more of the following steps:
closure of said valve 21;
activation of the first vibrator means 5;
further rotation of said support means 3 to position a new empty form below said discharge mouth 20.

Opportunely, the device 1 comprises a PLC (programmable logic controller) that allows the various components of the device 1 to be managed. In particular, via this PLC the user can decide whether to control the device in manual mode—i.e. the machine waits for an input from the user before performing any operation or in automatic mode—i.e. the machine performs the various steps in succession at a presettable speed—.

Opportunely, the method of use of the device 1 comprises one or more of the following phases:
positioning the first zone 31 and the first form below said discharge mouth 20;
making the concrete flow through said discharge mouth 20 until the first form is full;
rotating the support means 3 to position a second form placed in said second zone 32 of the support means 3 below the discharge mouth 20;
making the concrete flow through said discharge mouth 20 until the second form is full;
possibly repeating the two preceding step with at least one other form;
vibrating the contents of at least the first and/or second form; typically, this step vibrates the support means 3 (in this case the contents of all the forms placed on the support means 3 are vibrated; this enables the concrete to be compacted).

Advantageously, after the step of making the concrete flow into the first form, but before vibrating the contents of the first form, the step is provided of passing the upper edge of the first form under the scraper 7, the latter levelling the quantity of concrete that bulges upwards from the first form. This levelling step occurs during rotation of the support means 3 intended to position the second form under the discharge mouth 20 or during further rotation of the support means 3. This levelling step is then repeated also for the other forms placed on the support means 3.

Opportunely, the method provides for positioning and/or removing the first form or the specimen contained therein from the support means 3 when the first form is placed at a zone of the device 1 in which it is not mounted by the hopper 200. For this purpose, the support means 3 are opportunely rotated. Advantageously, this can also be rotated with the positioning/removal of the other forms or of the specimens contained therein.

The invention that is thus conceived allows multiple advantages to be obtained.

Above all, it allows productivity to be increased in view of the high speed of production of the specimens. This also enables the time of a specialized technician to be reduced, which has not insignificant costs. Secondly, it reduces the risk of error in forming specimens as there is a high degree of automation. A further advantage is that it assists in the work of forming the specimens so that this operation would become performable also by personnel with fewer technical skills and less experience. A further advantage is that it reduces the physical effort required of the operator.

The invention that is thus conceived is susceptible to numerous modifications and versions, all of which are comprised within the inventive concept that characterizes the invention. Further, all the details are replaceable by other technically equivalent elements. In practice any materials and dimensions can be used, depending on need.

The invention claimed is:
1. A device for forming concrete specimens comprising:
concrete feeding means (2) comprising a discharge mouth (20);

support means (3) suitable for supporting at least a first and/or a second form, said discharge mouth (20) and the force of gravity directing the concrete flowing out of the feeding means (2) towards said support means (3);

first vibrator means (5) suitable for generating the vibration of at least the contents of the first and/or second form;

the concrete feeding means comprising a tank that is intended for containing the concrete and which acts as a storage unit;

the support means (3) comprising a first and a second zone (31, 32) that are suitable for supporting respectively the first and second form; said feeding means (2) and said support means (3) being reciprocally movable so as to assume at least a first and a second configuration; in the first configuration said discharge mouth (20) and gravity directing the outflowing concrete towards said first zone (31), in the second configuration said discharge mouth (20) and gravity directing the concrete flowing out of the feeding means (2) towards said second zone (32);

the feeding means (2) comprising dosing means (9) for dosing the amount of concrete to allow to flow through the discharge mouth (20);

the tank of the feeding means (2) comprising:
  i) an exit opening (83) for the concrete which is connectable to said discharge mouth (20) through a conduit (84), the exit opening (83) for the concrete lying at one end of the conduit (84);
  ii) a lower bottom (82) which is raisable and lowerable with respect to the exit opening (83);, in at least one configuration the exit opening (83) being at a greater height than the lower bottom (82);

the dosing means (9) comprising means (85) for raising/lowering the bottom (82) of the tank.

2. The device according to claim 1, characterized in that the tank is a hopper (200); said hopper (200) and said support means (3) being reciprocally movable so as to also assume a third configuration in which at least a part of the first zone (31) extends outside the vertical projection of said hopper (200) on said support means (3) to facilitate the removal and positioning of said first form relative to the support means (3).

3. The device according to claim 1, characterized in that the device comprises a weight-bearing structure (6) supporting the feeding means (2) and the support means (3).

4. The device according to claim 3, characterized in that said weight-bearing structure (6) comprises facilitated sliding means (60) suitable for allowing the movement of the weight-bearing structure (6) on a surface outside the device (1).

5. The device according to claim 4, characterized in that said facilitated sliding means (60) are motorized.

6. The device according to claim 1, characterized in that said support means (3) comprise an element (33) rotating about a rotation axis.

7. The device according to claim 6, characterized in that the device comprises a scraper (7) positioned above said support means (3) and suitable for levelling the concrete which bulges out from said first form at least during a complete rotation of said element (33) rotating about said rotation axis.

8. The device according to claim 1, characterized in that the device comprises means (8) for positioning and at least partially retaining the first and/or second form on top of said support means (3).

9. The device according to claim 8, characterized in that:
  the support means (3) comprise a supporting base (34) on which said first and/or said second form are intended to rest;
  said positioning and at least partial retaining means (8) comprise a first collar (80) suitable for at least partially framing said first form, said first collar (80) being set at a distance from said supporting base (34).

10. The device according to claim 9, characterized in that said first collar (80) comprises a channel (81) suitable for collecting the concrete that comes out of the first form.

11. The device according to claim 1, characterized in that said first vibrator means (5) comprise a wall-mounted vibrator (50) that generates the vibration of said support means (3).

12. A device for forming concrete specimens comprising:
  concrete feeding means (2) comprising a discharge mouth (20);
  support means (3) suitable for supporting at least a first and/or a second form, said discharge mouth (20) and the force of gravity directing the concrete flowing out of the feeding means (2) towards said support means (3);
  first vibrator means (5) suitable for generating the vibration of at least the contents of the first and/or second form;
  the concrete feeding means comprising a tank that is intended for containing the concrete and which acts as a storage unit;
  the support means (3) comprising a first and a second zone (31, 32) that are suitable for supporting respectively the first and second form; said feeding means (2) and said support means (3) being reciprocally movable so as to assume at least a first and a second configuration; in the first configuration said discharge mouth (20) and gravity directing the outflowing concrete towards said first zone (31), in the second configuration said discharge mouth (20) and gravity directing the concrete flowing out of the feeding means (2) towards said second zone (32);
  the feeding means (2) comprising dosing means (9) for dosing the amount of concrete to allow to flow through the discharge mouth (20);
  the tank of the feeding means (2) comprising:
    i) a raisable and lowerable lower bottom (82);
    ii) an exit opening (83) for the concrete and which is connectable to said discharge mouth (20); the exit opening (83) being at a greater height than the lower bottom (82);
  the dosing means (9) comprising means (85) for raising/lowering the bottom (82) of the tank.

* * * * *